(12) United States Patent
Smith et al.

(10) Patent No.: US 6,293,929 B1
(45) Date of Patent: *Sep. 25, 2001

(54) WOUND IRRIGATION APPARATUS

(76) Inventors: Steven M. Smith, 1226 E. Second Ave., Salt Lake, UT (US) 84103; Mark A. Christensen, 1230 E. 100 S.; Philip M. Triolo, 148 S. 1200 E., both of Salt Lake, UT (US) 84102; Deborah K. Jacobson, 616 W. Briar Knoll Ct., Saukville, WI (US) 53080

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/925,866

(22) Filed: Sep. 9, 1997

Related U.S. Application Data

(60) Provisional application No. 60/057,321, filed on Sep. 2, 1997.

(51) Int. Cl.$^7$ ................................. A61M 35/00
(52) U.S. Cl. ................................................. 604/289
(58) Field of Search ................................ 604/263, 187, 604/268, 289, 296, 300, 312, 313, 315, 316, 192, 35, 36, 119, 116, 543; 128/917, 919, 846, 847, 849; 433/116

(56) References Cited

U.S. PATENT DOCUMENTS

| | | |
|---|---|---|
| D. 344,133 | 2/1994 | Stamler . |
| D. 345,016 | 3/1994 | Stamler . |
| 3,288,140 | 11/1966 | McCarthy . |
| 4,376,437 | 3/1983 | Sundheim et al. . |
| 4,692,140 | 9/1987 | Olson . |
| 4,769,003 | 9/1988 | Stamler . |
| 4,857,060 * | 8/1989 | Rosenberg . |
| 4,898,588 | 2/1990 | Roberts . |
| 5,224,940 | 7/1993 | Dann et al. . |
| 5,241,969 | 9/1993 | Carson et al. . |
| 5,248,307 | 9/1993 | Sokoloff . |
| 5,376,003 | 12/1994 | Rizkalla . |
| 5,441,174 | 8/1995 | Sperry . |
| 5,480,410 | 1/1996 | Cuschieri et al. . |
| 5,496,290 | 3/1996 | Ackerman . |
| 5,554,132 | 9/1996 | Straits et al. . |
| 5,624,419 | 4/1997 | Ersek et al. . |
| 5,735,833 * | 4/1998 | Olson .................................. 604/289 |
| 5,941,859 * | 8/1999 | Lerman ................................ 604/289 |

FOREIGN PATENT DOCUMENTS

| | | | |
|---|---|---|---|
| 0302762 * | 12/1936 | (IT) ....................................... | 604/116 |
| WO 97/48427 | 12/1997 | (WO) . | |

* cited by examiner

*Primary Examiner*—Sharon Kennedy
*Assistant Examiner*—Catherine Serke
(74) *Attorney, Agent, or Firm*—TraskBritt

(57) ABSTRACT

A wound irrigation apparatus comprising a fillable fluid delivery member, a fluid channel, and a splash shield for use in wound irrigation is disclosed. The splash shield is a three-dimensional shield positionable about a wound to protect medical personnel from the back splash resulting from wound irrigation and is at least partially flexible and compliant for shaping the shield to fit the unique shape or dimension of a wound. The flexible peripheral edge of the splash shield also prevents damage to the wound if the shield should come in contact with the wound. The shield may also be structured to provide selective angular adjustment of fluid delivery to the wound. The shield of the present invention generally comprises a shield member and a hub positioned through the surface of the shield member to direct fluid to a wound. The shield member may be structured to provide selective angular positioning of the hub to selectively direct fluid to the wound site. The fluid channel may be variable in length, internal diameter and bore shape to selectively determine the pressure at which fluid is delivered to the wound site and to selectively determine the spray pattern. The wound irrigation apparatus may also include an ergonomically designed handle attachable to the fillable fluid delivery member for facilitating filling and evacuation of the fluid delivery member.

7 Claims, 6 Drawing Sheets

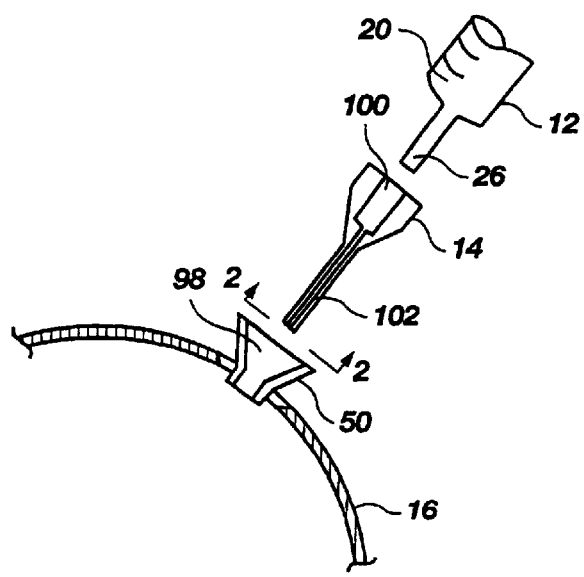
*Fig. 14*
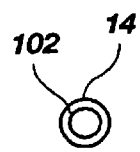   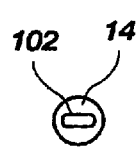   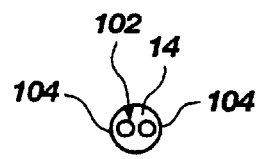
*Fig. 15A*   *Fig. 15B*   *Fig. 15C*
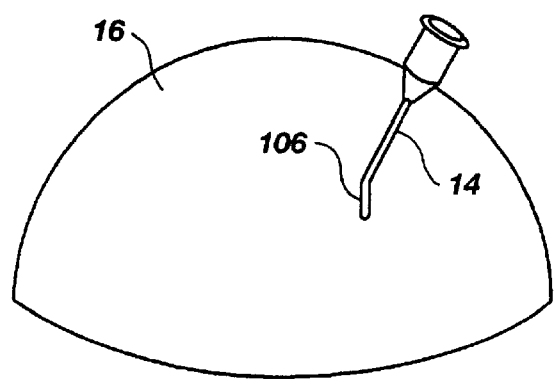
*Fig. 16*

WOUND IRRIGATION APPARATUS

CROSS REFERENCE TO RELATED APPLICATION

This application claims the benefit of U.S. Provisional Application No. 60/057,321, filed Sep. 2, 1997.

BACKGROUND

1. Field of the Invention

This invention relates to medical devices used in irrigating and cleansing wound sites on patients, and is specifically related to splash shields for preventing the back splash of fluids from a wound during wound irrigation so that the wound fluids do not contact the attending medical caregiver.

2. Statement of the Art

It is well-known that wounds to the body which occur through injury or accident, through surgical procedure, or which are caused by compromised circulation, such as pressure ulcers, must often be cleansed to keep the wound free of bacteria and other deleterious matter which may compromise the rate at which the wound heals. Cleansing of the wound often involves irrigating the wound with a stream or spray of liquid, such as isotonic saline or other sterile solution. Current clinical practice guidelines indicate that an irrigation pressure of between four to fifteen pounds per square inch pressure is effective for the cleansing of pressure ulcers or other chronic wounds. That amount of pressure is sufficient for removal of foreign particles, debris and bacteria to thereby promote healing and minimization of infection or inflammation, yet low enough to avoid or minimize damage to regenerating granulation tissue in the wound. The guidelines also recommend the use of high pressure irrigation for mechanical debridement, in which case there are no limitations to the maximum amount of pressure that may be used to remove the devitalized tissue.

Delivery of the irrigating liquid to the wound site is usually accomplished by pumping liquid from a hypodermic syringe through an attached needle, or syringe connector, trained toward the wound site. Most of the liquid delivered to a wound site flows away from the wound site, and is usually collected in some manner, such as in a bowl or with absorbent material. However, some back splash of fluid and debris from the wound occurs, especially at higher pressures of liquid delivery. The liquid back splash contains not only irrigating liquid, but fluid from the wound and loose matter extracted from the wound—particularly in situations where wound irrigation is conducted for debridement of the wound. It is unpleasant and potentially dangerous to have the back splash liquid from the wound strike the medical personnel conducting the irrigation procedure or the patient, or to have the material contaminate the environment. Current OHSA guidelines regarding blood-bourne pathogens require the minimization of the splatter and splashing of blood and the creation of aerosols containing potentially contaminated body fluids. Therefore, shield devices have been developed in the art to protect the caregiver from being exposed to the back splash.

Examples of wound irrigating back splash shields are disclosed in U.S. Pat. No. 4,692,140 to Olson, U.S. Pat. No. 4,669,003 to Stamler, U.S. Pat. No. 4,898,588 to Roberts, U.S. Pat. No. 5,224,940 to Dann et al., U.S. Pat. No. Des. 344,133 to Stamler, U.S. Pat. No. Des. 345,016 to Stamler, U.S. Pat. No. 5,376,003 to Rizkalla, U.S. Pat. No. 5,441,174 to Sperry and U.S. Pat. No. 5,496,290 to Ackerman. Most of the shields disclosed in the referenced patents are rigid and are, therefore, unadaptable to the variation in wound shapes which occur. As a result, back splash liquid can still escape the confines of such shields. More importantly, rigid prior art shields can damage the regenerating tissue of a wound if the rigid circumferential edge of the shield is pressed against, scraped along, or otherwise contacted with the wound.

Most of the shields disclosed in the referenced patents are configured with a liquid delivery conduit which is positioned in alignment with a central longitudinal axis of the shield so that liquid delivery is strictly along that central longitudinal axis. The configuration of such devices requires the fluid delivery apparatus (i.e., typically a hypodermic syringe) to be positioned in vertical alignment with the wound to effectuate liquid delivery. The placement or positioning of a wound on a patient is not always so accommodating. For example, a wound on the back of a patient who cannot be moved or rotated significantly from a supine position requires the caregiver to position himself and the irrigation device at a difficult angle to reach the wound. Furthermore, even those shields which are configured to provide a fluid conduit which is not strictly oriented along a longitudinal axis of the shield are unable to be angularly adjusted to modify the direction of liquid delivery to the wound.

Clinical practice guidelines requiring an irrigation pressure of 4 to 15 psi for the effective cleaning of wounds also imposes an additional requirement for wound irrigating devices which is not addressed in prior art devices. It is left to the judgment of the caregiver to determine when and if the irrigating fluid is being delivered to the wound within the required range of pressure. The failure to irrigate the wound at the appropriate fluid pressure can adversely affect the health and healing of the wound, and ultimately the patient. The importance of proper irrigation is further complicated by the fact that some patients, such as elderly or frail patients, often have wounds that do not heal or the tissue does not regenerate rapidly. Thus, fluid delivered at too high a pressure may compromise the healing process, and fluid deliberately delivered at a lower pressure may be inadequate for cleaning the wound.

Using conventionally known wound irrigating devices, the caregiver must depress with the thumb and fingers the plunger of a 35 cc hypodermic syringe filled with irrigating fluid and fitted with a 19 gauge needle of one and one half inches in length to produce an 8 psi delivery of irrigating fluid. That methodology assumes that all caregivers have the same degree of manual strength to depress the plunger and does not take into consideration that the caregiver's hand tires after repeated fillings and evacuations of the syringe in a single wound irrigating episode, thereby leading to less and less pressure being applied to depression of the plunger. Another factor leading to uneven or inconsistent fluid pressure at delivery is the mechanics of hand movement leading to different pressure being applied to the plunger when the plunger is fully extended from the syringe barrel (and the thumb is displaced farther from the fingers) as opposed to when the plunger is almost fully positioned in the barrel (and the thumb is closer to the fingers).

Thus, it would be beneficial to the art to provide a wound irrigation apparatus which facilitates delivering irrigation fluid at a specified pressure and which includes a splash shield which is safe for use in proximity to a wound, which is adaptable to the differences in wound dimension and body contour, and which provides a degree of angular adjustability to facilitate delivery of the irrigating fluid to a wound site while still providing protection from the back splash of fluid and other debris from the wound.

SUMMARY OF THE INVENTION

In accordance with the present invention, a wound irrigation apparatus is provided which facilitates the delivery of wound irrigating fluid to a wound site at a selected pressure, and includes a three-dimensional shield providing protection from back splash, the shield being at least partially flexible and compliant for shaping the shield to fit the shape or dimension of a wound and the contour of the body where the wound is located, to prevent damage to the tissues of the wound in case of contact with the wound and being structured to provide selective angular adjustment of fluid delivery to the wound. The wound irrigation device of the present invention generally comprises a fillable fluid delivery member, a fluid channel, an ergonomically shaped handle associated with the fluid delivery member and a splash shield structured to be at least partially flexible to provide selective angular positioning of a fluid channel to selectively direct fluid to the wound site.

The fillable fluid delivery member of the present invention may be any suitable device which has a volume that may be filled with irrigating fluid and which has means for evacuating the volume at will. The volume may preferably be refillable. The fillable fluid delivery member may have connected thereto an ergonomically designed handle which employs the strongest muscle groups of the arm and shoulder to facilitate quick and efficient filling of the fluid delivery member and subsequent evacuation of the fluid delivery member. Because the ergonomic handle may preferably use the force of the entire arm to deliver fluid from the fluid delivery member, the amount of pressure applied in the fluid delivery member is constant and consistent, thereby assuring a more constant and consistent fluid pressure at delivery. The handle may also enable fluid delivery at higher pressures than are achievable with conventional, single-handed delivery methods, and provides improved control so that fluid pressure at delivery may be selectively adjusted as required. The handle is designed, in the alternative, to be used in a conventional, single-handed delivery mode. The ergonomic design of the handle lessens fatigue in the hand and arm during fluid delivery.

The fluid channel of the present invention is positioned between the fillable fluid delivery member and the splash shield and directs irrigation fluid from the fluid delivery member to the wound site. The fluid channel may be affixed to the fluid delivery member or may be removably attached to the fluid delivery member, or it may be affixed to or removably attached to the splash shield. Any suitable fluid channel may be used which has a bore having at least two open ends. A conventional hypodermic needle having a selected gauge may be one suitable example. Preferably, the fluid channel is a needle-like member the bore size and length of which may be selected to deliver irrigating fluid therethrough at a selected pressure. The fluid channel may have a straight or linear bore, or the fluid channel may be non-linear or curved to facilitate the control of the fluid delivery within a defined area and to selectively control the pressure at which fluid is delivered to the wound site.

Further, the bore of the fluid channel may be formed as a conventional tube or cylinder so that the cross section shape of the bore is circular. Alternatively, the bore may be structured with any other shape or dimension of bore, such as oblong, square or rectangular, to selectively dictate the pattern of fluid spray emanating from the fluid channel. Alternatively, and preferably, the fluid channel is cylindrical, but the tip of the fluid channel is modified in cross sectional shape to be any other suitable shape, such as oval, oblong, square, etc., to provide a selectable spray pattern.

The fluid channel is preferably angularly adjustable, relative to the shield, to allow the user to selectively control the angle of spray and, therefore, the pressure at which fluid is delivered to the wound. It is notable that the pressure at which irrigating fluid is delivered to the wound site, within the protocol specified ranges, is determined, in the present invention, by the cross sectional area of the volume of the fillable fluid delivery member, the dimensions (i.e., the bore size, length and shape) of the fluid channel, the angle of orientation of the fluid delivery to the wound site and the cross sectional area of the evacuating means (e.g., the plunger head). By selectively varying one or more of those factors, the caregiver can deliver irrigating fluid to the wound site at a selected pressure within the specified protocol range of between 4–15 psi. A fluid delivery at 12 psi may be preferred.

The shield of the present invention may generally be hemispherical in shape, comprising a peripheral edge which is positionable near or against the patient's body and a substantially continuous dome-like surface extending upwardly therefrom. The peripheral edge, in lateral cross section, may be circular, oval, oblong or any other suitable shape. The shield member is formed at least partially of a flexible or compliant material which renders the shield member conformable to any shape or dimension of a wound and renders it conformable to the topography of the body. In those embodiments where the shield member is only partially made of a flexible material, the flexible or compliant portion is located near the peripheral edge of the shield member and the less flexible, or comparatively rigid, portion of the shield member is located away from the peripheral edge. Thus, the peripheral edge, in any embodiment of the invention, is flexible so that it can be manipulated to be formed about the unique shape or dimension of the wound and the body's contour and, more importantly, so that if the shield should come in contact with the wound, it will flex and not damage the tender tissues of the wound.

The shield may be structured in any suitable manner to be flexible at the peripheral edge, but substantially inflexible or comparatively rigid in other regions of the shield. The shield may then, for example, be formed by varying the thickness of the material from the apex of the shield to the peripheral edge, by fabricating the shield from materials having a different modulus of elasticity, by removing plasticizers from the material of the shield in the area where increased stiffness or rigidity is desired, by adding plasticizers in areas where flexibility is desired or using reinforcing longitudinal ribs incorporated into the material or structure of the shield. The peripheral edge of the shield member may be planar (i.e., every point along the entire peripheral edge would contact a planar surface) to contain more back splash liquid in the shield, or the peripheral edge may be non-linear, such as being scalloped, to allow fluid to exit between the peripheral edge of the shield member and the patient's skin. Additionally, a plurality of small, deformable openings may be formed through the surface of the shield member to allow fluid displacement in the shield.

The shield of the invention may, in one embodiment, be wholly flexible throughout the structure thereby providing the greatest degree of manipulation of the shield to fit the shape or dimension of the wound and the contour of the body. The shield of the invention, in another embodiment, may be partially flexible and partially inflexible or comparatively rigid. In either embodiment, the shield may be structured to receive or retain the fluid channel so that irrigating fluid is delivered through the surface of the shield and to the wound. In one embodiment of the invention, the shield may be whole and imperforate, having markings along the outer surface thereof to direct the placement of the fluid channel therethrough. In such an embodiment, the fluid channel may typically be a needle or needle-like member having a tip or edge sufficiently sharp to pierce the shield at any one of the designated markings. The markings may include a marking at the apex of the shield and at various locations extending along a line from the apex to near the peripheral edge of the shield. In this embodiment, the fluid channel is of sufficient length to extend through the surface of the shield, but not beyond the peripheral edge of the shield.

In another embodiment of the invention, the shield may be formed with perforated circular sections which, when punctured by the fluid channel, are released from the surface of the shield leaving an opening sized to receive the fluid channel or a portion of the fillable fluid delivery member therethrough. The perforated circular sections may be formed at the apex of the shield and at various points extending in a line from the apex of the shield to its peripheral edge. In still another embodiment of the invention, the surface of the shield may be formed with one or more pre-punched or formed holes sized to receive the fluid channel or a portion of the fillable fluid delivery member therethrough. In this embodiment, it may be preferable that only one hole be formed in the surface of the shield, either at the apex of the shield or at any location along a line extending from the apex to near the peripheral edge of the shield, and the caregiver can simply select a shield having the pre-punched hole formed at the desired location. In any of the previously described embodiments, the shield is structured to be flexible in the area immediately surrounding the point at which the fluid channel is inserted through the surface of the shield. Thus, the angle of the fluid channel, relative to the surface of the shield, may be modified to selectively deliver fluid to the wound site at a desired angle.

In yet another general embodiment of the invention, the shield may be formed with a hub positioned along or through the surface of the shield to either receive or retain the fluid channel therethrough. The hub may, in one embodiment, be generally formed with a collar which is sized to receive or engage a portion of the fillable fluid delivery member and/or the fluid channel. In one embodiment, the collar of the hub may be formed as a female Luer-type fitting sized to engage the male Luer fitting of a conventional syringe (also referred to herein as "the syringe hub"), and is also formed with a channel fitting sized to receive the fluid channel, or needle, of the syringe. In such cases, the syringe may serve as the fillable fluid delivery member and the needle of the syringe serves as the fluid channel. In an alternative embodiment of the invention, the hub of the shield member is formed with a collar sized to engage a portion of the fluid delivery member, such as the male Luer fitting of the syringe hub, but the fluid channel is formed with the hub of the shield member, thereby eliminating the need for use or insertion of a needle connected to the fillable fluid delivery member. In this embodiment, the fluid channel of the hub may be permanently integrated or connected with the hub. In the alternative, the fluid channel may be replaceable with interchangeable fluid channels having different bore and/or bore tip shapes or configurations to provide a variety of different spray patterns, as previously described.

The hub of the shield member may be located at the center or apex of the shield member. Alternatively, and preferably, the hub of the shield member may be located away from the center or apex of the shield so that the fluid is delivered to the wound site at an angle to a longitudinal axis oriented perpendicularly to the plane of the peripheral edge of the shield member. In any embodiment of the invention, the area of the shield member immediately surrounding the hub is structured to allow the hub to be rotated relative to the shield member so that the angle at which liquid, moving through the hub from the fillable fluid delivery member, may be selectively modified. By so configuring the shield member of the present invention, the angle at which irrigating liquid is delivered to the wound site may be selected in accordance with the unique requirements of the wound (e.g., shape, depth, dimension, sensitivity). That is, some wounds are shallow and the tissues are delicate so that the delivery of liquid in a directly vertical orientation to the wound, particularly at higher pressures, may cause tearing of the delicate tissues. Delivering liquid at an angle to the wound is less traumatic to the tissues, even at elevated pressure levels, and modifying the direction or angle of the spray insures that the entire area of the wound can be bathed with irrigation fluid at a desired pressure. It may be particularly suitable to form the shield member with angle indicia near the hub of the shield member to direct the user in appropriately modifying the angle of the spray.

In yet another embodiment of the invention, the hub may be formed with an elongated body which, at the distal end, forms a fluid channel directing liquid to the wound site and, at the proximal end, is formed with a conduit fitting sized to engage a portion of the fillable fluid delivery member. The body of the hub also includes a secondary fluid channel connected to a tube which may be inserted into a source of irrigation liquid, such as a bottle. A valve system is positioned in the body of the hub. Thus, when liquid is to be delivered to the wound site, the plunger of a syringe or similar device, which is attached to the hub, is withdrawn from the barrel of the syringe providing sufficient negative pressure to draw liquid from the liquid source through the tube and into the syringe via the hub. The valve system operates under the negative pressure created by the plunger of the syringe to prevent fluid from being aspirated from inside the shield member or from the wound site. Liquid is then delivered through the hub of the shield member and to the wound site by pushing the plunger of the syringe back into the barrel of the syringe. The valve system then operates to effectively close the secondary fluid channel under the force of fluid pressure and allows the liquid to move through the fluid channel to the wound site.

These features of the present invention may be more fully understood when considered in connection with the following description of the illustrated invention.

BRIEF DESCRIPTION OF THE DRAWINGS

In the drawings, which illustrate what is currently considered to be the best mode for carrying out the present invention:

FIG. 14 is a view in cross section of an alternative embodiment of the hub of the shield member configured with a replaceable fluid channel;

FIGS. 15A, 15B and 15C are alternative end views of the fluid channel shown in FIG. 14, taken at line 2—2;

FIG. 16 is a perspective view of a shield member having an alternatively designed fluid channel associated therewith;

DETAILED DESCRIPTION OF THE ILLUSTRATED EMBODIMENTS

Figure 1:
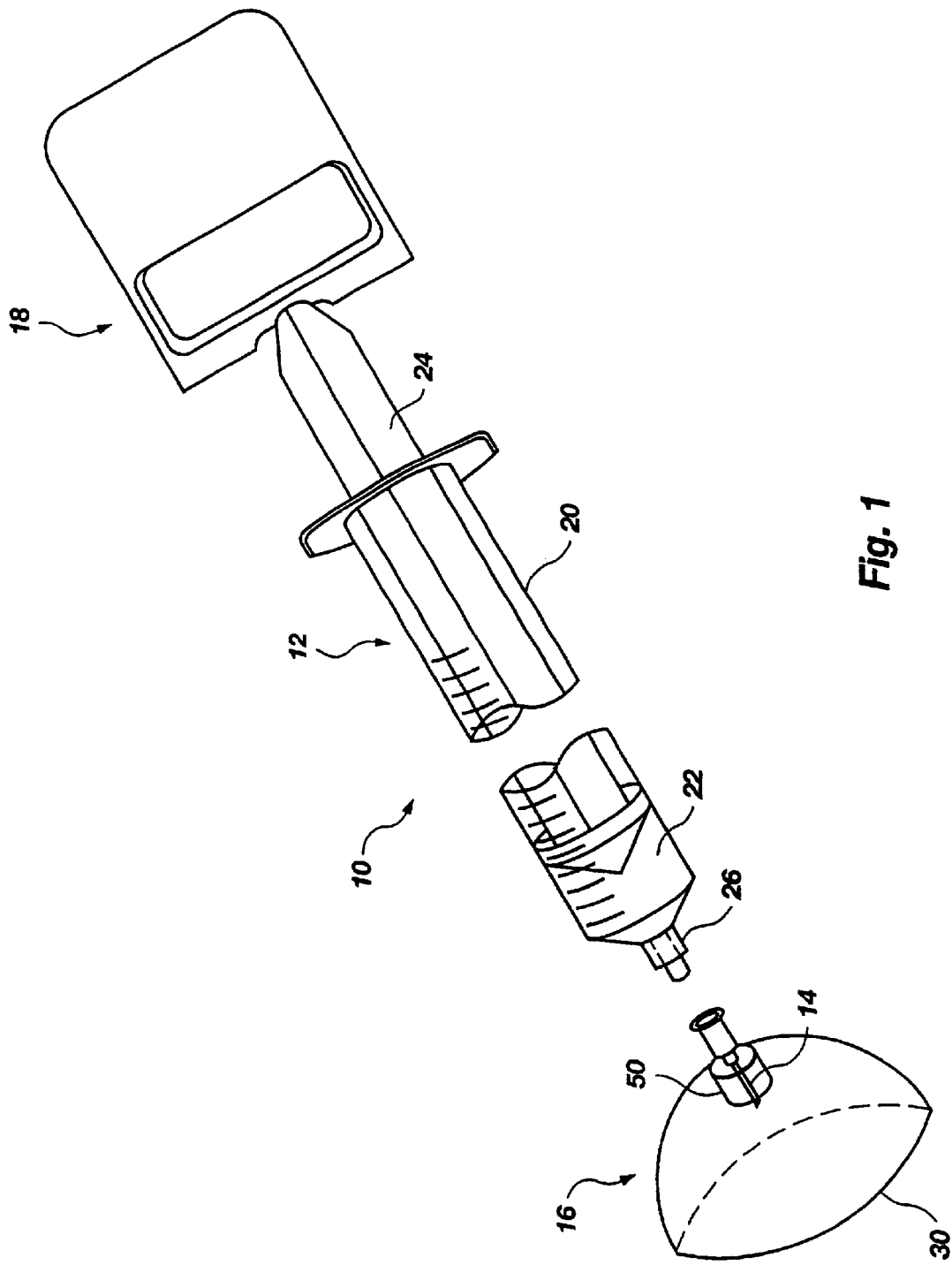
FIG. 1 is a perspective view of the wound irrigation apparatus of the present invention.

The basic elements of the wound irrigation apparatus 10 of the present invention are shown in FIG. 1. The invention generally comprises a fillable fluid delivery member 12, a fluid channel 14, a shield member 16 and an ergonomically designed handle 18. The fillable fluid delivery member 10 may be any suitable device which has a volume capable of being filled with irrigation fluid and being subsequently evacuated. An example of a suitable such device is shown in FIG. 1 as a syringe 20 having a hollow barrel 22, a movable plunger 24 and a syringe hub 26 for connecting a needle hub thereto. The syringe hub 26 may be formed in any suitable manner, but is shown in FIG. 1 as a male Luer fitting. The shield member 16 is a three-dimensional structure formed, at least in part, of a flexible or pliant material which is preferably substantially transparent so that the user can see the wound site located beneath the shield member 16 during use. The shield member 16 may be formed of any number of suitable materials, including polyvinyl chloride, polyurethane, silicone rubber or other thermoplastic elastomers. The fluid channel 14 is generally positioned between the fluid delivery member 12 and the shield member 16 to convey irrigation fluid from the fluid delivery member 12 to the wound site positioned beneath the shield member 16. The handle 18 is designed to facilitate filling and evacuation of the fluid delivery member 12 using the major muscle groups of the arm and shoulder. Both the fluid channel 14 and handle 18 are described in greater detail below.

Figure 8:
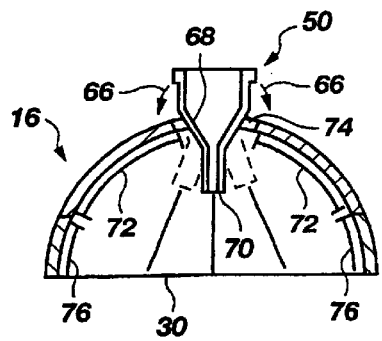
FIG. 8 is a view in cross section of an alternative embodiment of the shield member which is partially flexible and partially inflexible.
Figure 10:
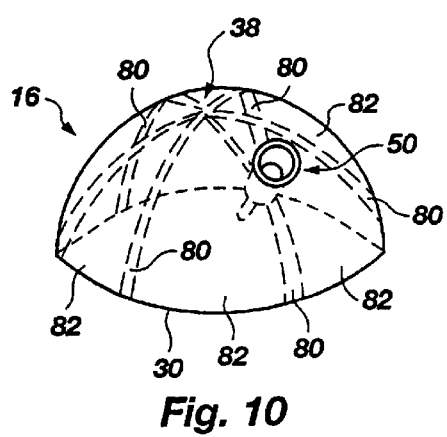
FIG. 10 is a perspective view of an alternative embodiment of the present invention where the shield member is partially flexible and stability is imparted to the shield member by the formation of longitudinal ribs in the shield member.
Figure 9:
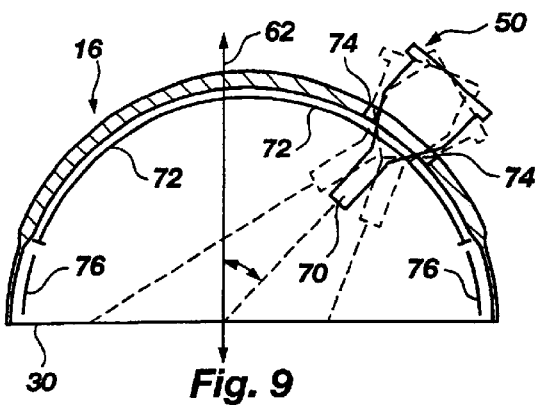
FIG. 9 is a view in cross section of an alternative embodiment of the invention where the shield member is partially flexible and formed of varying thickness, and the hub is positioned at an angle to the longitudinal axis of the shield member.

The three-dimensional shield member 16 of the present invention is generally hemispherical in shape, as shown throughout the illustrations of this disclosure, but may take any suitable form, size, shape, dimension or design which prevents back splash of irrigating fluid and wound fluid or debris. In principal, the shield member 16 may be structured as a wholly flexible form, such as those embodiments shown in FIGS. 3–7, or the shield member 16 may be partially flexible and partially inflexible or comparatively rigid, as shown in FIGS. 8–10. In either a wholly or partially flexible embodiment, the shield member 16 is formed to be flexible at the peripheral edge 30 (FIG. 1) of the shield member 16 to enable manipulation of the peripheral edge 30 to fit the unique shape or dimension of a wound and the contour of the patient's body and, more importantly, to prevent damage to the sensitive wound area if the peripheral edge 30 should come in contact with the wound. It is also a principal element of the present invention that the shield member 16 be formed so that the immediate area about which the fluid channel 14 is positioned at or through the shield member 16 is flexible so that the angle or orientation of the fluid channel 14 relative to the wound and to the shield member 16 can be selectively modified.

Figure 2:
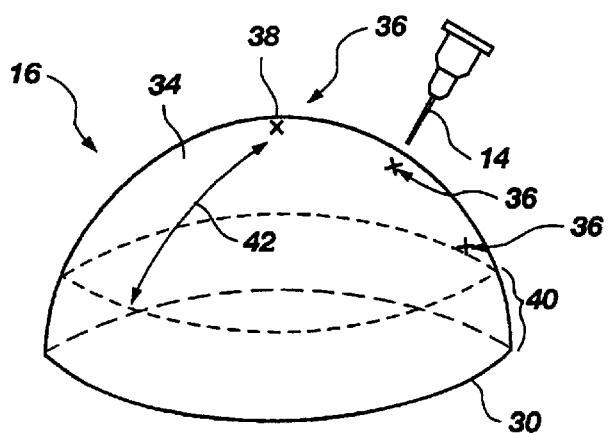
FIG. 2 is a perspective view of a first embodiment of the shield member which is imperforate.

In a first embodiment of the invention shown in FIG. 2, the shield member 16 may be formed as a completely imperforate, three-dimensional form having a peripheral edge 30 and an outer surface 34 extending therebetween with a series of markings 36 appearing on the outer surface 34 of the shield member 16. The markings 36 may preferably include a marking at the apex 38 of the shield member 16 and a plurality of markings extending in a line from the apex 38 of the shield member 16 to the peripheral edge 30. The markings indicate where the user may puncture or insert the fluid channel 14 through the imperforate form to position the fluid channel 14 for delivery of irrigating fluid to the wound site.

In the embodiment shown in FIG. 2, for example, the shield member 16 may be wholly flexible or may, as shown, be formed with a width 40 of flexible material extending a distance from the peripheral edge 30. The portion 42 of the shield member 16 extending from the flexible width 40 to the apex 38 of the shield member 16 may be substantially inflexible or comparatively rigid, except for the area immediately around the markings 36 (which may be formed as thin sections of material), which enables not only the puncturing of the surface 34 of the shield member 16, but enables manipulation of the fluid channel 14 to selectively modify the angle of orientation at which the irrigating fluid is delivered to the wound site.

Figure 3:
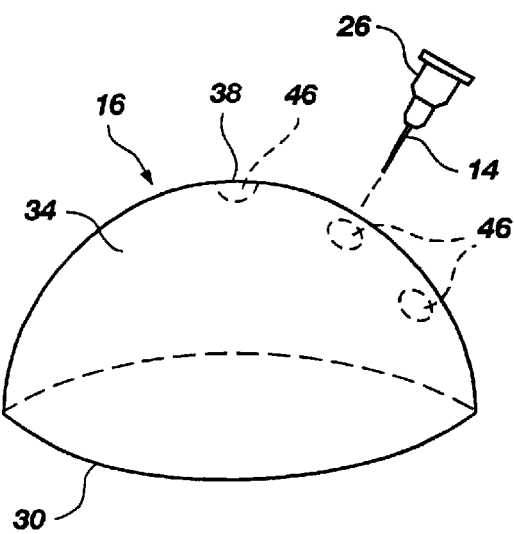
FIG. 3 is a perspective view of another embodiment of the shield member having perforated sections.

In an alternative embodiment shown in FIG. 3, the shield member 16 may be formed with perforated circular sections 46 which, when pressed by the fluid channel 14, will release from the surface 34 of the shield member 16, thereby providing a hole sized for receiving the fluid channel 14 therethrough. The perforated circular sections 46 may be positioned at the apex 38 of the shield member 16 and along a line extending from the apex 38 of the shield member 16 to near the peripheral edge 30. The embodiment of the invention shown in FIG. 3 enables the user to select the desired angle at which the fluid channel 14 is oriented to the wound site. As previously noted, the area immediately surrounding perforated sections 46 may be flexibly formed to allow the fluid channel 14 to be manipulated to selectively modify the angle at which the fluid channel 14 is oriented relative to the wound site.

Figure 4:
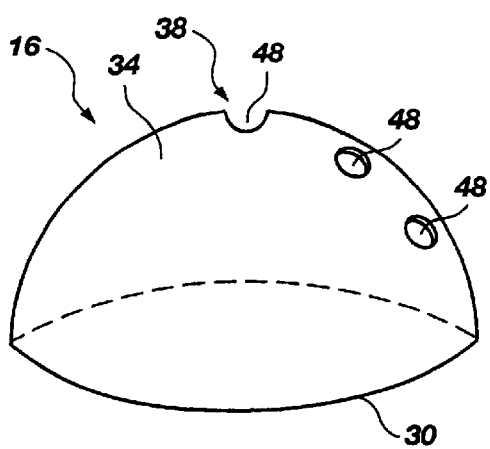
FIG. 4 is a perspective view of another embodiment of the shield member having preformed or pre-punched holes.

In another alternative embodiment of the invention shown in FIG. 4, the shield member 16 may be formed with a preformed or pre-punched hole 48 through the surface 34 of the shield member 16. The hole 48 is preferably sized to receive the fluid channel (not shown) therethrough. The pre-punched hole 48 may be located at the apex 38 of the shield member 16 or along a line extending from the apex 38 of the shield member 16 to the peripheral edge 30. Although the shield member 16 is shown in FIG. 4 with a plurality of holes 48 it may be preferable that only one pre-punched hole 48 be formed in the shield member 16 so that fluid does not escape through other larger sized holes 48 formed in the shield member 16.

Figure 5:
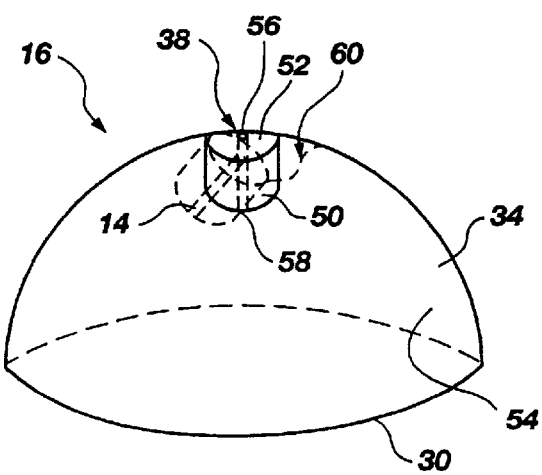
FIG. 5 is a perspective view of yet another alternative embodiment of the shield member having a hub which extends into the interior space of the shield member, and the fluid channel is integrally formed with the hub.

In another general embodiment of the invention, illustrated in FIGS. 5–14, the shield member 16 of the invention may include a hub 50 which is generally structured to receive or retain the fluid channel 14 therethrough. The hub 50 may be formed along the surface of the shield member 16 or through the shield member 16. In the embodiment of the shield member 16 shown in FIG. 5, the hub 50 comprises a cylindrically-shaped disk 52 secured to the inside surface 54 of the shield member 16. The disk 52 may be located at the apex 38 of the shield member 16, as shown, or may be located at a position other than at the apex 38. The disk 52 may be formed with a bore 56 sized in cross sectional dimension and length to slidingly receive the fluid channel (not shown) therein. Alternatively, and as shown in FIG. 5, the bore 56 may serve as the fluid channel and is, therefore, integrally formed in the disk 52. The fluid channel 14 preferably does not extend more than a few millimeters from the bottom end 58 of the disk 52 to lessen any likelihood that the fluid channel 14 would contact the wound site. As previously noted, the area of the shield member 16 immediately about the hub 50 is flexible thereby allowing selective modification of the angle at which the fluid channel 14 is directed toward the wound site. This principle is illustrated in FIG. 5 where it can be seen in phantom line that the area 60 of the shield member 16 about the hub 50 may deform or deflect so that the hub 50 angle may be modified, as also shown in phantom.

Figure 6:
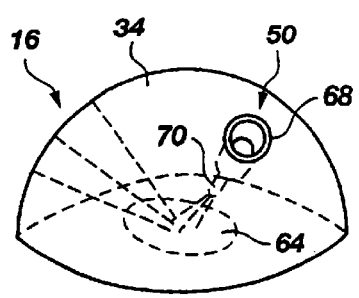
FIG. 6 is a perspective view of another embodiment of the shield member formed with a hub positioned through the shield member and at an angle to deliver fluid to a wound site.
Figure 7:
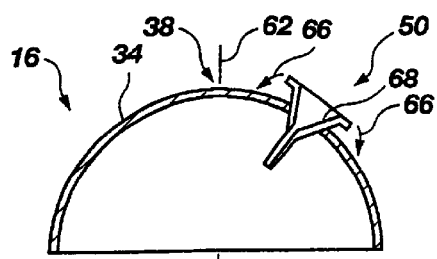
FIG. 7 is a view in cross section of the embodiment shown in FIG. 6.

As shown in FIGS. 6 and 7, the hub 50 may alternatively be positioned through the surface 34 of the shield member 16, and at an angle to a longitudinal axis 62 formed through the central apex 38 of the shield member 16. Positioning the hub 50 at an angle to the longitudinal axis 62 of the shield member 16 allows irrigating fluid to be delivered to the wound site 64 at a selected angle, rather than directly on the wound site 64. By selectively positioning the hub 50 at an angle to the wound site 64, damage to the tender tissues of the wound can be avoided, and directing the back splash at a given angle to the wound can be more easily controlled. The area of the shield member 16 immediately surrounding the hub 50 is particularly structured to permit the hub 50 to move angularly, in the direction of arrows 66, relative to the surface 34 of the shield member 16. As a result, the angle of the hub 50 relative to the longitudinal axis 62 of the shield member 16 can be selectively modified to deliver irrigating fluid to the wound site 64 at a desired angle.

The selective adjustability of the hub 50 relative to the shield member 16 also allows the user to direct the spray of irrigating fluid over the entirety of the wound site 64 without moving the shield 16. This factor provides a significant advantage over prior shield devices for wound irrigating systems because they are fixed in direction, usually directing liquid along the longitudinal axis of the shield, and the shield must be moved about the wound site to direct irrigating liquid to various points of the wound site. More importantly, however, the ability to modify the angle of the hub 50, and, therefore, the direction of the spray toward the wound enables the irrigation and cleansing of wounds which are situated in areas of the patient's body which are hard to reach by the medical caregiver, such as wounds located on the back of a bedridden patient or on the heel of the foot.

The hub 50 of the embodiment illustrated in FIGS. 6 and 7 is generally comprised of a collar 68 which is sized to engage a portion of the fillable fluid delivery member 12 (not shown), such as, for example, the syringe hub. The collar 68 may, in one embodiment, be formed as a female Luer fitting so that it may engage the male Luer fitting of a syringe hub 26 (shown in FIG. 1). The collar 68 is connected to a bore 70 which is sized to slidingly receive a fluid channel 14 (not shown), such as, for example, a needle attached to the syringe hub 26. The fluid channel 14 may, in this embodiment, be associated with the fillable fluid delivery member 12.

The pliant nature of the shield member 16, as stated previously, permits the manipulation of the shield member 16 to conform to the shape or dimension of a particular wound site 64 or the contour of the body. The pliant nature of the shield member 16 also provides selective adjustment of the hub 50 as previously described. However, the construction of the shield member 16 may be modified to provide some substantial rigidity to the shield member 16. As shown in FIG. 8, the shield member 16 may be modified, for example, with an upper section 72 which is inflexible or substantially rigid. The upper section 72 may extend from an area above, and distanced from, the peripheral edge 30 of the shield member 16 to the hub 50 or to the hub area 74 located immediately about the hub 50. As shown in the embodiment of FIG. 8, the hub 50 is located near the apex 38 of the shield member 16 and the hub area 74 is located about the apex 38 of the shield member 16. The hub area 74, when included, is flexible to permit angular movement of the hub 50, in the direction of arrows 66, as suggested by the different angular positions of the bore 70 shown in phantom in FIG. 8. The lower section 76 of the shield member 16, located at the peripheral edge 30 of the shield member 16 and extending a distance away from the peripheral edge 30, is flexible and pliant to allow the shield member 16 to be positioned about the wound site 64 as previously described, and to avoid damage to the wound if contact with the wound site 64 should be made. The embodiment of the shield member 16 shown in FIG. 8 may, for example, be formed by adding plasticizers to the shield member 16 in the area of the lower section 76 to render that section more flexible, or plasticizers may be removed from portions of the upper section 72 to render it substantially rigid.

In another embodiment, shown in FIG. 9, the shield member 16 is formed with an upper section 72 which is comparatively rigid, but for a hub area 74 located immediately about the hub 50 which is flexible and permits movement of the hub 50 relative to the shield member 16 to selectively modify the direction of the spray of irrigating fluid moving through the fluid channel 14 (not shown) positioned through the bore 70 of the hub 50. In the embodiment shown in FIG. 9, the hub 50 is located at an angle to the longitudinal axis 62 of the shield member 16 so that irrigating liquid may be directed toward a wound site at an angle thereto. The hub area 74 of the shield member 16 permits the angle of the hub 50 to be selectively modified so that the direction of spray of the irrigating fluid can be changed.

The embodiments shown in FIGS. 8 and 9, having an upper section 72 with a certain comparative rigidity or inflexibility and a lower section 76 having a certain flexibility, can be manufactured in any suitable manner to provide the disclosed structure. By way of example, the shield member 16 shown in FIG. 9 may be formed with varying degrees of thickness such that the upper section 72 is of greater thickness than the lower section 76 as a result of depositing more layers of material on the upper section 72 of the shield member 16. The variable thickness thereby renders the upper section 72 more inflexible than the lower section 76. Alternatively, the shield member 16 may be formed, such as by press molding, from materials having different moduli of elasticity such that the material in the upper section 72 has a higher modulus of elasticity than does the material of the lower section 76. Still alternatively, the shield member 16 shown in FIG. 8 may be made, for example, of a hardened or rigid plastic material, but a plasticizing agent may be added to the lower section 76 of the shield member 16 to render it more flexible. Alternatively, the shield member 16 may be formed of a more flexible material, but the plasticizers are removed from those areas of the shield member 16, such as the upper section 72, which require higher inflexibility or greater rigidity. Likewise, the intended area for placement of the hub 50, or the hub area 74 of the shield member 16 may be treated with a plasticizer to impart a degree of flexibility to the hub area 74 thereby permitting movement of the hub 50 when secured in place through the surface 34 of the shield member 16. Other equally suitable means of forming the shield member 16 as illustrated in FIGS. 8 and 9 are available, including molding or coating.

In another embodiment of the invention shown in FIG. 10 some longitudinal rigidity may be provided in the shield member 16 by incorporating longitudinal rib members 80 into the shield member 16. The longitudinal rib members 80 extend from the apex 38 of the shield member 16 to the peripheral edge 30 thereof. The rib members 80 may be made of substantially rigid, or only slightly flexible, plastic strips which are incorporated into the flexible plastic material of the shield member 16, or the rib members 80 may be formed by treating longitudinal sections of the shield member 16, which is made of a hardened plastic, with a plasticizer to render sections 82 of the shield member 16 flexible. Alternatively, the rib members 80 may be formed by increasing the thickness of longitudinal sections of the shield member 16. The hub 50 may be positioned through flexible sections 82 of the shield member 16, as shown, to permit the angle of the hub 50 to be selectively modified as previously described. In the alternative, the hub 50 may be positioned through the apex 38 of the shield member 16 when the shield member 16 is configured with a hub area which imparts a degree of flexibility to the shield member 16 about the hub 50 so that the angle of the hub 50 may be modified as described.

Figure 11:
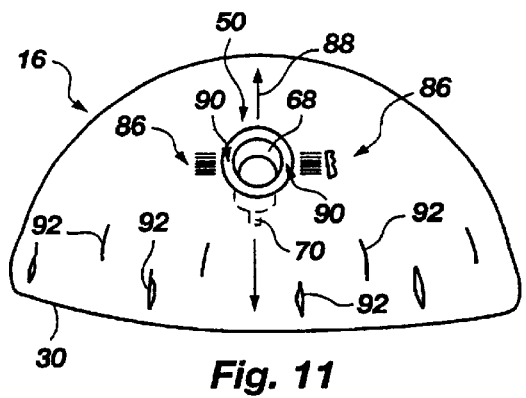
FIG. 11 is a perspective view of the invention illustrating indicia of angular degrees to which the hub may be moved, and deformable openings are formed near the peripheral edge of the shield member.

In a particularly suitable embodiment of the invention, illustrated in FIG. 11, the outer surface 34 of the shield member 16 may bear indicia 86 in close proximity to the hub 50 to assist the user in determining a desired change in the angle of spray of the irrigating liquid as the angle of the hub 50 is modified in the direction of arrows 88. Further, the collar 68 of the hub 50 may bear an appropriate mark 90 which assists in aligning the collar 68 with the indicia 86 on the surface 34 of the shield member 16 to achieve a desired angle of spray. The indicia 86 may, for example, be marked in degrees of angularity (e.g., 90°, 60°, 45°) relative to the longitudinal axis 62 of the shield member 16. The indicia 86 may also, for example, be marked with increments of length (e.g., −6 mm, −4 mm, −2 mm, 0, 2 mm, 4 mm, 6 mm) to indicate the distance from the longitudinal axis 62 the spray is being directed. Any form of indicia may be used, however.

Figure 12:
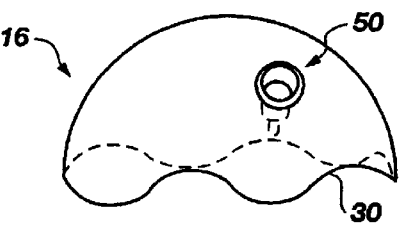
FIG. 12 is a perspective view of the invention illustrating a modification of the peripheral edge of the shield member.

Other modifications may be made to the basic shield member 16, including the overall shape of the shield member 16. The shield member 16 is shown in the several figures of this disclosure as being generally dome-shaped and the peripheral edge 30 being circular. However, other equally suitable shapes or dimensions may be employed and the "resting" shape of the peripheral edge may be oval, oblong or some other suitable configuration. Further, as illustrated in FIG. 11, the shield member 16 may be modified in the area of the peripheral edge 30 with a plurality of small, deformable openings 92 sized to allow the passage of liquid therethrough. The deformable openings 92 may be slits formed through the surface of the shield member 16 which open to varying degrees upon vertical compression of the shield member 16, as depicted in FIG. 11. The deformable openings 92 provide a means by which irrigating liquid may drain from inside the shield member 16 to an appropriate collecting device, such as a bowl or a towel. Another modification that may be made to the basic design of the shield member 16 is illustrated in FIG. 12 where the peripheral edge 30 is formed with a scalloped edge which allows the irrigating liquid to drain away from the wound site. Notably, the peripheral edge 30 of the embodiments shown in FIGS. 2–11 is planar, in that every point of the peripheral edge 30 will contact a plane formed along the edge of the shield member 16 at the peripheral edge 30. Other modifications may be made to the peripheral edge 30 to permit irrigating liquid to drain from the wound site such as, for example, notches or slits.

Figure 13:
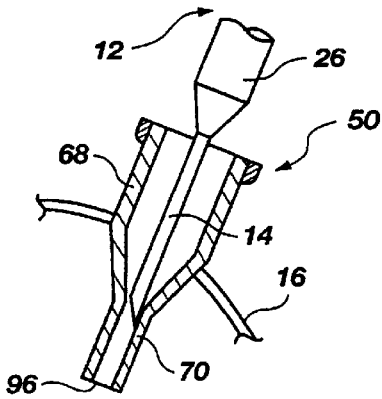
FIG. 13 is a view in cross section of one embodiment of the hub of the shield member configured to receive the needle and connector of a conventional syringe.

The hub 50 of the shield member 16 may be formed in a number of ways to bring irrigating liquid from the fillable fluid delivery member 12 to the wound site via the fluid channel 14. Thus, for example, as shown in FIG. 13, the hub 50 may be structured with a collar 68 which is sized to snugly engage a portion of the fillable fluid delivery member 12, such as the syringe hub 26 of a conventional hypodermic syringe, as shown. The hub 50 may also be formed with a bore 70 sized to slidably receive the fluid channel 14, which may, as illustrated, be a needle attached to the syringe hub 26. Thus, in this embodiment, the irrigating fluid moves from the fillable fluid delivery member 12 through the fluid channel 14 positioned in the bore 70 of the hub 50 and is directed to the wound site. In this embodiment, the fluid channel 14 may extend beyond the tip 96 of the bore 70 of the hub 50, but does not extend beyond the plane of the peripheral edge 30 of the shield member 16. This protects the wound from coming in contact with the sharp tip of a needle and prevents the caregiver from stabbing himself with the tip of the needle. Alternatively, the bore 70 of the hub 50 may be sized in length to be co-extensive with the length of the fluid channel 14, and is, therefore, not sized in length to extend beyond the plane of the peripheral edge 30 of the shield member 16.

In an alternative embodiment of the hub 50 shown in FIG. 14, the hub 50 may be formed with a collar fitting 98 which is sized to snugly and slidingly receive a replaceable or interchangeable fluid channel 14. The fluid channel 14 may further comprise a mechanical connector 100 for engaging a portion of the fillable fluid delivery member 12, such as, for example, the syringe hub 26 of a syringe 20. The fluid channel 14 also includes a bore 102 of selected internal diameter, shape and length.

The embodiment of the hub 50 shown in FIG. 14 is particularly suitable for the shield member 16 of the invention since the replaceable or interchangeable fluid channel 14 can be configured with any selected length, any selected measure of internal diameter or cross sectional shape of the bore to selectively dictate the pressure at which irrigating fluid is delivered to a wound site. As a general principle the longer the length of the bore 102 and the larger the internal diameter of the bore 102, the lower the fluid pressure may be as it is delivered through the fluid channel 14, all other factors being equal. The bore 102 of the fluid channel 14 may also be formed in a variety of different shapes, as viewed in cross section of the bore 102, thereby providing different spray patterns. Alternatively, just the tip of the bore 102 may be modified in shape to provide selected spray patterns. Thus, as shown in FIG. 15A, the bore 102 of the fluid channel 14 may, for example, be sized as a conventional cylindrical lumen to direct a linear stream, or conical-shaped spray, to the wound site. Alternatively, as shown in FIG. 15B, the tip of the bore 102 may be oblong or oval in lateral cross section to provide a thin, fan-like spray. In the alternative, as shown in FIG. 15C, the bore 102 may be formed with multiple numbers of cylindrical channels 104 which provide a full fan-like spray. Many other bore 102 sizes, shapes and numbers may be provided to control the type of spray delivered to the wound site.

The embodiment illustrated in FIG. 14 provides a hub 50 structured to engage a removable and replaceable fluid channel 14. However, in an alternative embodiment shown in FIG. 1, the fluid channel 14 may be integrally or permanently formed with the hub 50. In such an embodiment, the user may select that shield member 16 having a fluid channel 14 formed therewith which has the desired bore length, internal diameter size and bore shape to deliver a spray of irrigating fluid at a selected pressure and in a selected spray pattern. As noted previously, the shield member 16 is also structured to provide selected modification of the angle of the hub, and thus the fluid channel 14, relative to the wound site.

The fluid channel 14 of the present invention may be further modified to selectively determine the pressure at which irrigating fluid is delivered to the wound site and to selectively determine the angle at which irrigating fluid is delivered to the wound site. That is, in each of the embodiments described heretofore, the fluid channel 14 has been illustrated as being linear or straight along its length. However, as shown in FIG. 16, the fluid channel 14 may be configured to be non-linear along its length, thereby being formed with a bent or angled section 106. Bending or otherwise modifying the length of the fluid channel 14 modifies the pressure at which irrigating fluid can be delivered therethrough, and that factor may be used by the caregiver in selecting the appropriate fluid channel 14, in concert with the size and volume capacities of the fillable fluid delivery member 12. Also, bending the length of the fluid channel 14 further modifies the angle at which the irrigating fluid is delivered to the wound site.

Figure 17:
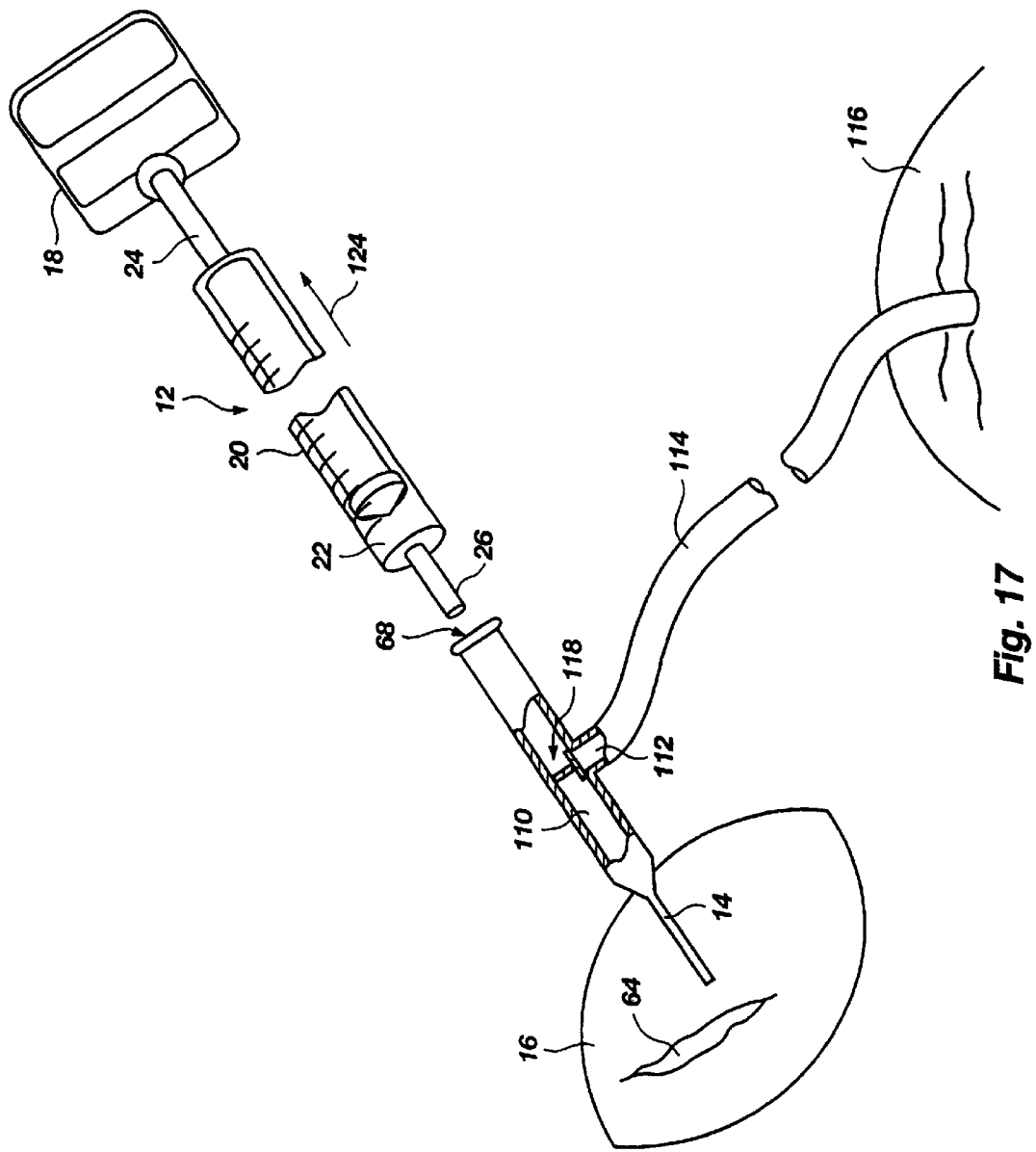
FIG. 17 is a perspective view, in partial cutaway, of an alternative embodiment of the hub of the shield member which is configured with a secondary fluid conduit for bringing liquid under suction pressure from a liquid source.

In yet another alternative embodiment of the invention shown in FIG. 17, the hub 50 may be formed with an extended fluid conduit 110 which is integral with and extends from the shield member 16 to the collar fitting 68. The collar fitting 68 is sized to snugly and slidably engage a portion of the fillable fluid delivery member 12, here shown as a syringe 20 having a syringe hub 26, a hollow barrel 22 providing a fillable volume, and a plunger 24. The collar fitting 68 may be formed, for example, as a female Luer-type fitting sized to engage the male Luer fitting of the syringe hub 26. The hub 50 of this embodiment is also formed with a secondary fluid conduit 112 which is in fluid communication with the extended fluid conduit 110 of the hub 50. The secondary fluid conduit 112 is formed with, or connected to, a tube 114 which is sized in length to connect to a source 116 of irrigating liquid. A valve system 118 is located in the extended fluid channel 110 of the hub 50 to allow passage of liquid in the direction of the wound site only. The valve system 118 also operates to allow fluid to be withdrawn from fluid source 116. The valve system may comprise one or more pressure relief valves or two check valves, or any other suitable device or arrangement. A pressure relief valve is shown in FIG. 17.

In operation, when irrigating liquid is to be delivered to the wound site 64, the plunger 24 of the syringe 20 is withdrawn, in the direction of arrow 124, by pulling on handle 18. Liquid is thereby drawn from the liquid source 116 through tube 114 via the secondary fluid conduit 112, then into the extended fluid conduit 110 and into the barrel 22 of the syringe 20. The valve system 118 remains closed under the negative pressure exerted by the movement of the plunger 24 so that substantially no liquid is withdrawn from beneath the shield member 16 or from the wound site 64. When irrigating liquid is to be delivered to the wound site 64, the handle 18 is pushed, thereby forcing the plunger 24 into the syringe barrel 22 and forcing the irrigating fluid through the extended fluid conduit 110, through the valve system 118 and to the fluid channel 14 to the wound site 64. During evacuation of the barrel 22, the valve system 118 is forced into a closed position relative to the secondary fluid conduit 114 to prevent irrigating fluid from being forced back to the source 116 of the fluid but remains open relative to the fluid channel 14. The process of filling and evacuating the fillable fluid delivery member 12 may be repeated continuously as needed. This embodiment is especially beneficial in providing a constant source of irrigating liquid to the device.

Figure 18:
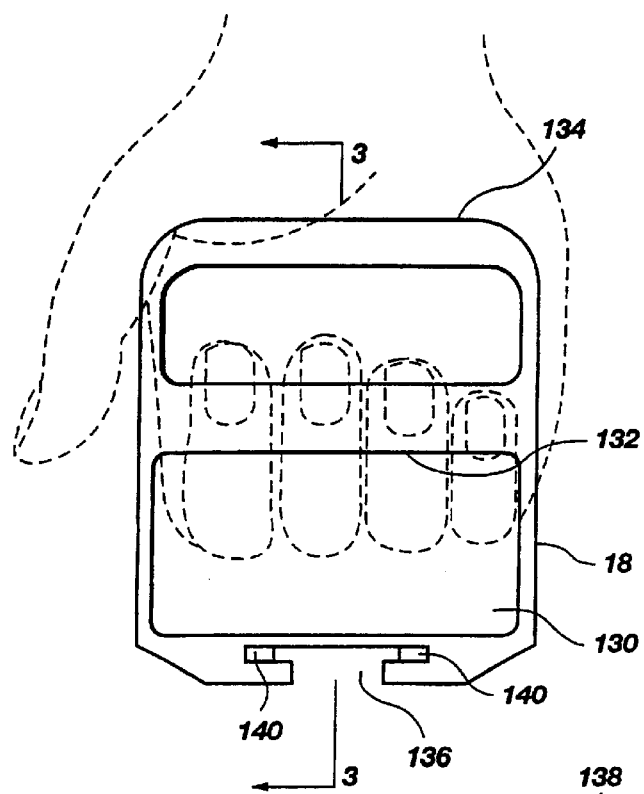
FIG. 18 is a view in elevation of the ergonomic handle of the present invention.

As described previously, the wound irrigation apparatus 10 may include an 134 ergonomically designed handle 18 which is structured to allow the caregiver to grasp the handle 18 with the entire hand, as illustrated in FIG. 18. By being able to grasp the handle 18 with the entire hand, the caregiver may employ the larger muscle groups of the arm and shoulder, such as the triceps and biceps, to quickly and easily fill the volume of the fillable fluid delivery member 12. More importantly, the handle 18 allows the use of the major muscle groups of the arm and shoulder during evacuation of the fillable fluid delivery member 12, which facilitates a more consistent and constant application of pressure to the volume leading to delivery of the irrigating fluid at a more constant pressure. The handle 18 may generally be formed with an opening 130 sized to receive the fingers of the hand therethrough. A lower ridge 132 located at one end of the opening 130 provides a surface about which the fingers may wrap, as shown. An upper ridge, spaced apart from the lower ridge 132, provides a surface against which the heel of the hand may rest. It can be seen, therefore, that the hand can securely engage the handle 18 thereby facilitating movement of a plunger or similar device.

Figure 19:
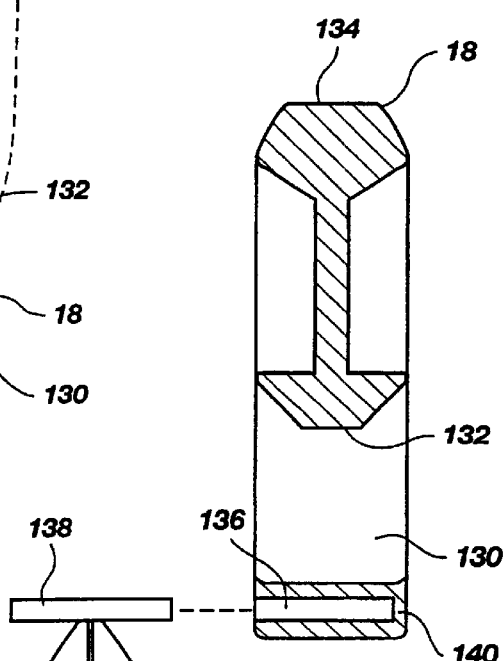
FIG. 19 is a view in cross section of the handle of FIG. 18, taken at line 3—3.
Figure 20:
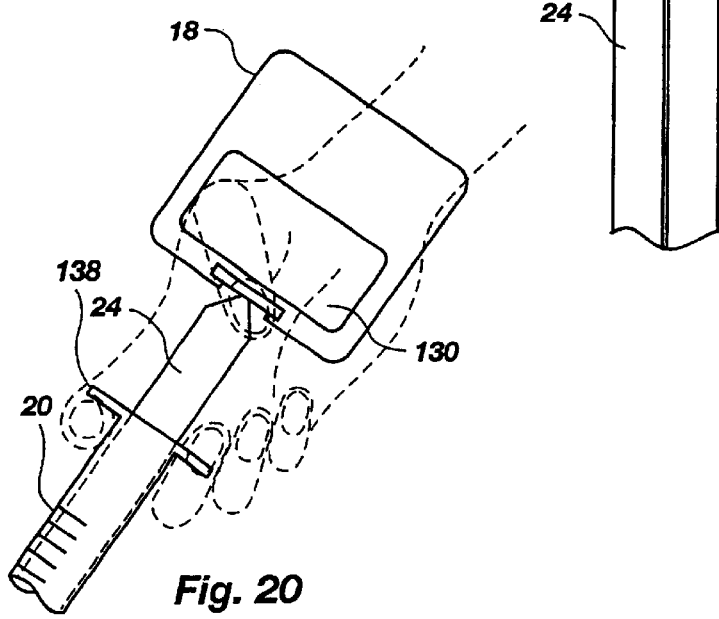
FIG. 20 is a view in elevation of the handle attached to the plunger of a syringe, illustrating a single-handed manipulation of the handle.

The handle 18, as shown in FIGS. 18 and 19, may be formed with a slot 136 sized to slidingly receive the end flange 138 of a plunger 24 of a conventional syringe. The end flange 138 of the plunger slides into the slot 136 a distance before it contacts an end surface 140 which prevents the flange 138 from sliding completely through the slot 136. Alternatively, as shown in FIG. 1, the handle 18 may be integrally formed with the plunger 24, or any similar device associated with the volume of the fillable fluid delivery member 12 for evacuating the volume of fluid. The handle 18 is particularly suitable for use in a two-banded manipulation of the fillable fluid delivery member 12 and handle 18 where, for example, the fillable fluid delivery member is cradled in the palm of the left hand and the handle 18 is grasped by the fingers and palm of the right hand. Two-handed use of the wound irrigation apparatus 10 provides the greatest amount of control in delivering fluid to the wound site at a selected pressure. However, in the alternative, the handle 18 may be adapted for conventional, one-handed use as shown in FIG. 20. That is, the thumb may be positioned through the opening 130 while the index finger and middle finger of the hand engage the end flange 138 of the plunger 24.

The wound irrigation device disclosed herein can be used in a selective combination of elements to achieve a given fluid pressure during delivery of irrigation fluid to the wound site. The following table demonstrates exemplar combinations of elements, using a standard hypodermic syringe, which achieve a given fluid pressure when the syringe is evacuated at a given time interval.

TABLE 1

| Syringe Capacity | Fluid Channel Dimension | Spray Pattern | Plunger Insertion Times and Corresponding Pressures of Irrigating Fluids at Orifice | | | | |
|---|---|---|---|---|---|---|---|
| | | | 4 Seconds | 6 Seconds | 8 Seconds | 10 Seconds | 12 Seconds |
| 30 cc | .042 inch i.d. | Jet | 12 psi | 8 psi | 6 psi | 4.8 psi | 4 psi |
| 30 | $1.4 \times 10^{-3}$ in.$^2$ | Fan | 12 | 8 | 6 | 4.8 | 4 |
| 30 | .027 inch i.d. | Jet | 24 | 16 | 12 | 9.6 | 8 |
| 30 | $5.7 \times 10^{-4}$ in.$^2$ | Fan | 24 | 16 | 12 | 9.6 | 8 |

Shaded areas represent pressures recommended by AHCPR guide}ines for cleansing of pressure ulcers It can be seen, therefore, that the syringe capacity (i.e., cross sectional area of the barrel), the dimensions of the fluid channel and the spray pattern add to the factors which maximize use of the present invention for wound irrigation. Although many different sizes or dimensions of elements may be used, in combination, to achieve a given fluid delivery pressure, it may be particularly suitable to employ a syringe having a capacity of between 25 cc to 35 cc in combination with a fluid channel the cross sectional area of the tip (i.e, the internal diameter or i.d.) of which ranges between about $4.9 \times 10^{-4}$ inches$^2$ to about $6.6 \times 10^{-4}$ inches$^2$ when achieving a fluid pressure of 12 psi and ranges between about $1.26 \times 10^{-3}$ inches$^2$ to about $1.52 \times 10^{-3}$ inches$^2$ to achieve a fluid pressure of 6 psi. These exemplar dimensions assume a fluid evacuation from the syringe at between a 4 to 12 second time interval.

The wound irrigation apparatus of the present invention is structured to provide delivery of irrigation fluid to a wound site at a selected pressure, which may be selectively modified by the caregiver's selection of a fillable fluid delivery member with a given cross sectional area, selection of the shape and dimension of the fluid channel, selection of the rate of plunger insertion in the syringe barrel (i.e., fluid evacuation), selection of a given shape and configuration of the splash shield. The splash shield of the present invention is particularly suitable for wound irrigation because of its flexible or partially flexible character which allows the peripheral edge of the shield to be readily shaped or manipulated to accommodate the shape or dimension of a wound or body contour and to avoid harmful contact with the wound. The splash shield of the present invention is further uniquely structured to provide selective modification of the angle at which irrigating fluid is delivered to the wound site to provide better coverage and less movement of the shield to meet the shape or dimension requirements of the wound. The splash shield may be modified to accept irrigating fluid from any suitable source and the hub may be modified accordingly. Thus, reference herein to specific details of the illustrated embodiments is by way of example and not by way of limitation. It will be apparent to those skilled in the art that many modifications of the basic illustrated embodiment may be made without departing from the spirit and scope of the invention as recited by the claims.

What is claimed is:

1. A splash shield for use in wound irrigation comprising:
   a three-dimensional shield having a flexible continuous peripheral edge for orienting toward a patient's body in a non-sealing and form-complying manner, a surface extending therebetween forming a domed member, of uniform thickness in crosssection an apex and a longitudinal axis extending therethrough, said domed member having a first portion which is flexible and a second portion which is relatively less flexible than said first portion; and
   at least one access positioned on said domed member through which fluid may be delivered to beneath said domed member, of said domed member an area immediately surrounding said at least one access being flexible and pliant to provide movement of said at least one access relative to said domed member.

2. The splash shield of claim 1 wherein said at least one access is an opening formed through the surface of said domed member and positioned at said apex.

3. The splash shield of claim 1 wherein said at least one access is a rigid hub positioned on said domed member, said hub having a fluid channel through which fluid is deliverable to beneath said domed member.

4. The splash shield of claim 3 wherein said hub is positioned at said apex.

5. The splash shield of claim 1 wherein said first portion is located at said continuous peripheral edge and said second portion extends from above said first portion to proximate said at least one access.

6. The splash shield of claim 1 wherein said first portion is a lower section extending from said continuous peripheral edge toward said apex, and said second portion is an upper section extending from said lower section to near said apex, the relative flexibility of said lower section being different from the flexibility of said upper section.

7. A splash shield for use in wound irrigation comprising:
- a three-dimensional shield having a flexible continuous peripheral edge for orienting toward a patient's body in a non-sealing and form-complying manner, a surface extending therebetween forming a domed member, an apex and a longitudinal axis extending therethrough, said domed member having a first portion which is flexible and a second portion which is relatively less flexible than said first portion; and
- at least one access positioned on said domed member through which fluid may be delivered to beneath said domed member, said domed area being flexible and pliant in an area immediately surrounding said at least one access to provide movement of said at least one access relative to said domed area;

wherein said first portion is a lower section of said shield extending from said continuous peripheral edge toward said apex, and said second portion is an upper section of said shield extending from said lower section to near said apex, the thickness in cross section of said domed member in said lower section being the same as the thickness in cross section of said domed member in said upper section, said lower section being of different flexibility relative to said upper section.

* * * * *